United States Patent
Troyansky et al.

(10) Patent No.: US 7,610,324 B2
(45) Date of Patent: Oct. 27, 2009

(54) SYSTEM FOR DETECTION AND ESTIMATION OF PERIODIC PATTERNS IN A NOISY SIGNAL

(76) Inventors: Lidror Troyansky, 18 Jabotinsky St., Ramat Gan (IL) 52505; Arnon Breuer, 18 Hassidey Umot Haolam St., Haifa (IL) 32985

( * ) Notice: Subject to any disclaimer, the term of this patent is extended or adjusted under 35 U.S.C. 154(b) by 1191 days.

(21) Appl. No.: 10/885,605

(22) Filed: Jul. 8, 2004

(65) Prior Publication Data
US 2005/0033146 A1 Feb. 10, 2005

(51) Int. Cl.
*G06F 17/15* (2006.01)
(52) U.S. Cl. ...................... 708/422; 708/426
(58) Field of Classification Search ............... 708/422, 708/426
See application file for complete search history.

(56) References Cited

U.S. PATENT DOCUMENTS

| 5,596,371 A * | 1/1997 | Pakhchyan et al. ......... 348/452 |
| 2004/0008160 A1 * | 1/2004 | Etheridge et al. ........... 345/30 |

* cited by examiner

*Primary Examiner*—Tan V Mai

(57) ABSTRACT

A method for the detection and estimation of periodicities in noisy signals. First the signal is sampled and preprocessed in a discrete succession of equal periods. Then, short term characteristics vectors are generated for each period. The short term characteristics vectors are then grouped into sets, followed by the obtainment of at least one representative vector for each set. Periodic structures are estimated using the representative vectors. In a preferred embodiment, the short term characteristics are the the short term spectra of the signal. Practically, an autocorrelation matrix is constructed to assess autocorrelation along a diagonal.

14 Claims, 8 Drawing Sheets

SYSTEM FOR DETECTION AND ESTIMATION OF PERIODIC PATTERNS IN A NOISY SIGNAL

FIELD OF THE INVENTION

The present invention relates generally to the field of signal processing.

More specifically, the present invention is a methodical approach for detecting periodic and quasi-periodic patterns in noisy signals.

BACKGROUND OF THE INVENTION

Periodic structures are common in natural systems as well as in man made systems. Examples in natural systems are cyclical activity of the biological systems such as the cardio vascular network and the respiratory system. Astronomical systems exhibit periodic phenomena of which the motion of planets is well known. Technological systems are often associated with periodic phenomena, well known are oscillating electronic circuits associated with cyclic transformation of energy and mechanical engines associated with cyclical transformation of chemical to mechanical energy. The analysis of periodicities in systems may provide a key to understanding functional aspects of systems. For example, deviations from the standard cyclical mode can provide insight into the nature of a defect occurring in the system. Thus a malfunctioning valve is a source of a deviation from a standard cyclical pattern of an internal combustion engine. In the medical practice, the correlation existing between the electrical ECG signal and the mechanical cyclical pattern of the heart is a source of information that can be taken to describe the well-being of the cardiac system.

The most prevalent methods for the detection and estimation of periodic phenomena are based on spectral estimation. In general spectral estimation analyses techniques are applied that are equivalent to a Fourier transform of the auto-correlation of the signal. In such an analysis only the instantaneous amplitude of the signal is taken into account. There are cases, however, in which the instantaneous amplitude of the signal does not reveal any clear periodicity, as can be seen in FIGS. 1A-B to which reference is now made. In FIG. 1A a spectrogram of a frequency modulated periodic signal is shown. In FIG. 1B the power spectrum of the spectrogram is shown that does not reveal a periodic structure. In cases where the periodic structures are frequency modulation or amplitude modulations, de-modulation of the signal is necessary before further estimation of periods. The problem becomes more involved in the presence of noise.

For natural signals, periodic structure can be of more subtle nature then plane amplitude or frequency modulation: e.g., the signal may include periodic structures that involve a combination of amplitude and frequency modifications, as well as phase-shifts, in the presence of noise. In other cases, the periodic structure may be composed of modulations (amplitude and/or frequency modulations) of noise, as is the case in some mechanical systems.

There is thus a recognized need for, and it would be highly advantageous to have, a method that allows for reliable estimation of periodic structures in an intricate signal, which will overcome the drawbacks of current methods as described above.

SUMMARY OF THE INVENTION

The present invention provides a novel method for detection and estimation of intricate periodicities in signals. The signal is sampled and subsequently processed in discrete, equally spaced, slices of time. A vector of characteristics is extracted for each such time slice and the vectors are grouped into sets, each having an initial time and period. Various statistics for each set, such as the mean, variance or entropy are estimated, corresponding to various periods. When a periodic structure exits, the statistics estimated in the corresponding interval become more pronounced, thereby indicating the existence of the corresponding periodic structure.

DETAILED DESCRIPTION OF THE PRESENT INVENTION

Figure 1A:
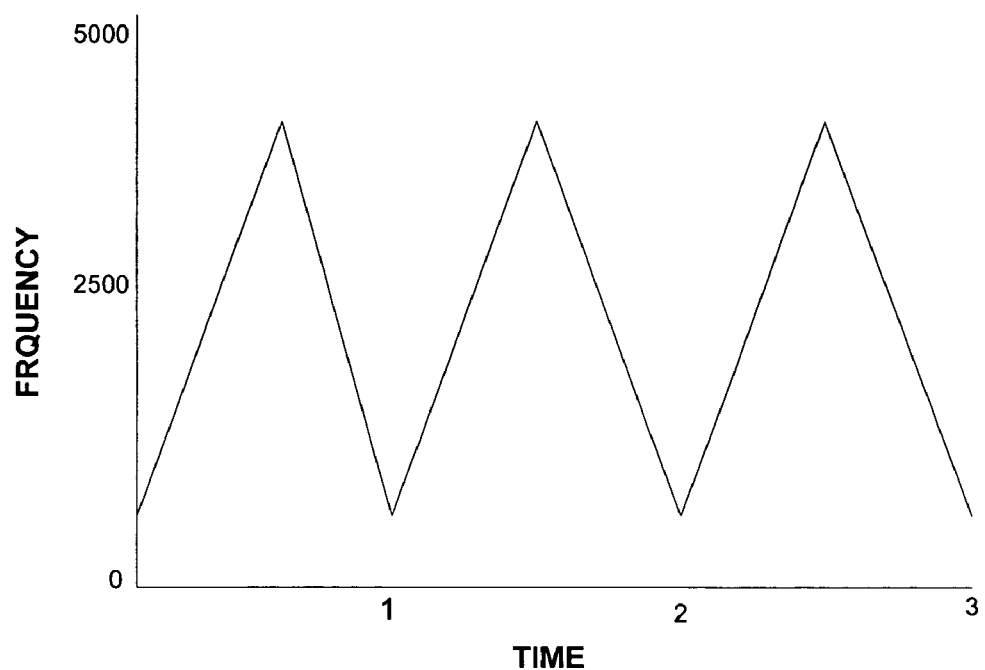
FIG. 1A is a spectrogram of a frequency modulated periodic signal.
Figure 1B:
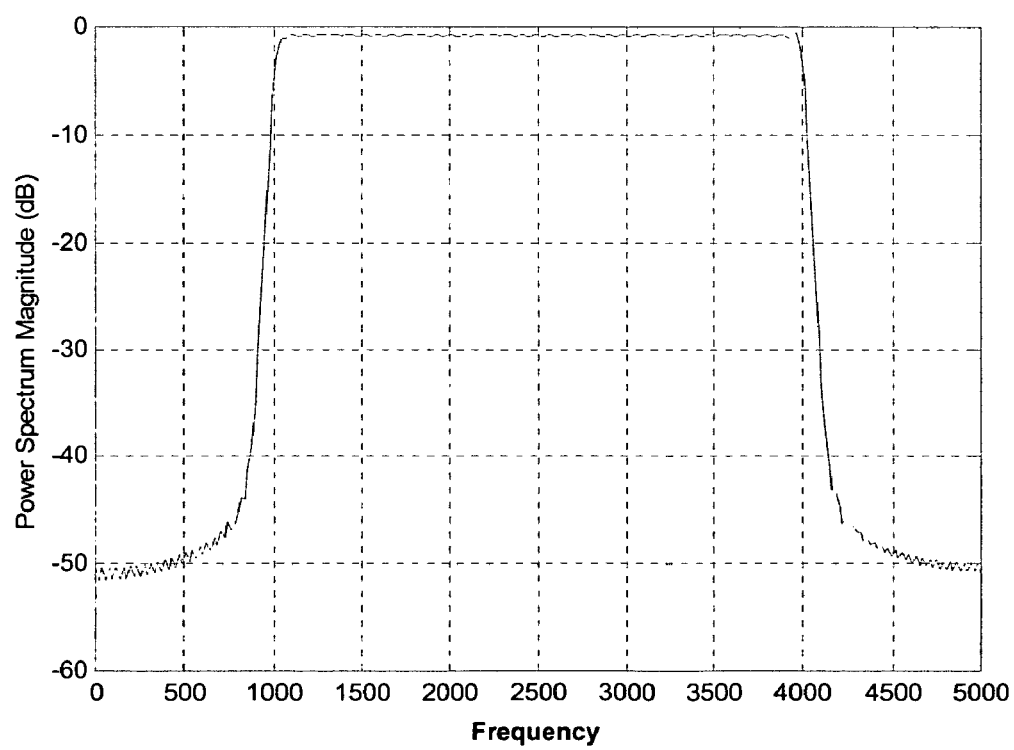
FIG. 1B is a power spectrum of the spectrogram of FIG. 1B.
Figure 2:
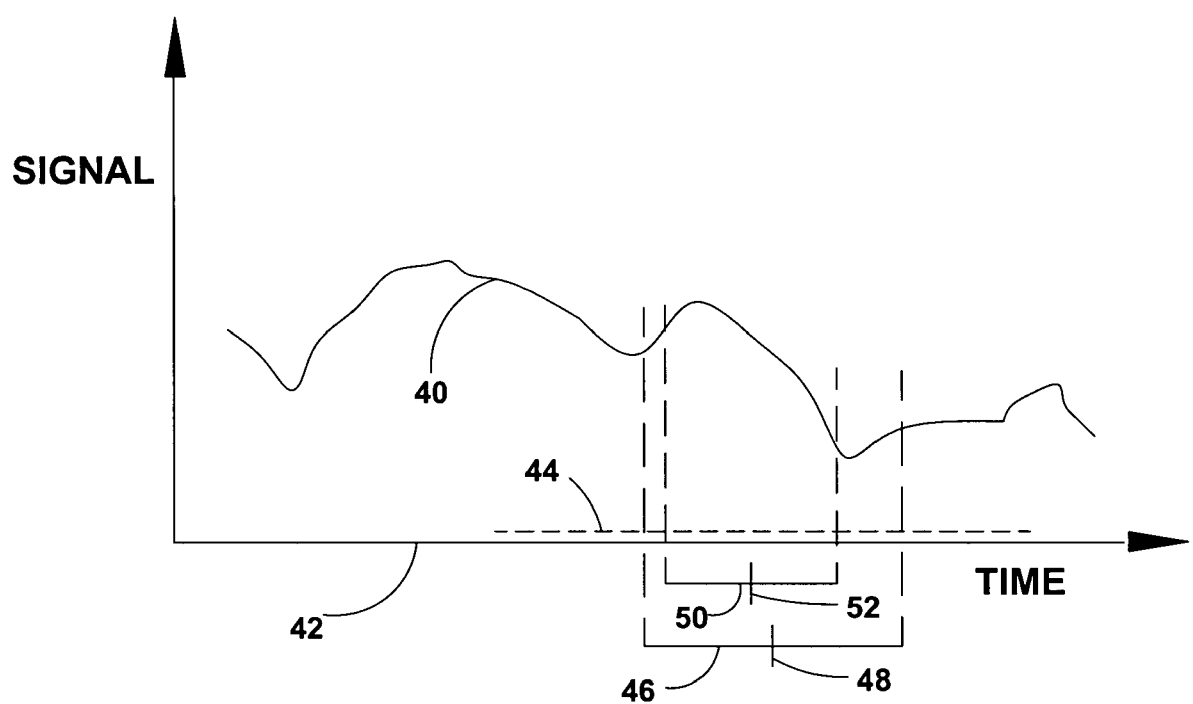
FIG. 2 is a schematic description of a discrete time slice implemented in the processing of a signal in accordance with the present invention.

In accordance with the present invention, intricate periodicities can be discerned in a signal by applying a procedure as set out in the following description. Such a procedure is performed by a dedicated or a general purpose hardware as will be described further. In accordance with the invention, the signal is sampled and subsequently processed in discrete slices of time. One such discrete slice of time is described schematically in FIG. 2 to which reference is now made. Signal 40, appearing as a variations of amplitude over the time (or space) axis 42, is sampled in a succession of discrete quanta of time described schematically by dashed line 44. Discrete time slice 46 is typified by its length and by its central time value 48. Discrete time slice 50 is an example of a shorter slice having a central time value 52. The length of the slice of time is typically predetermined by a reference to the nature of the periodicity sought-after.

Figure 3A:
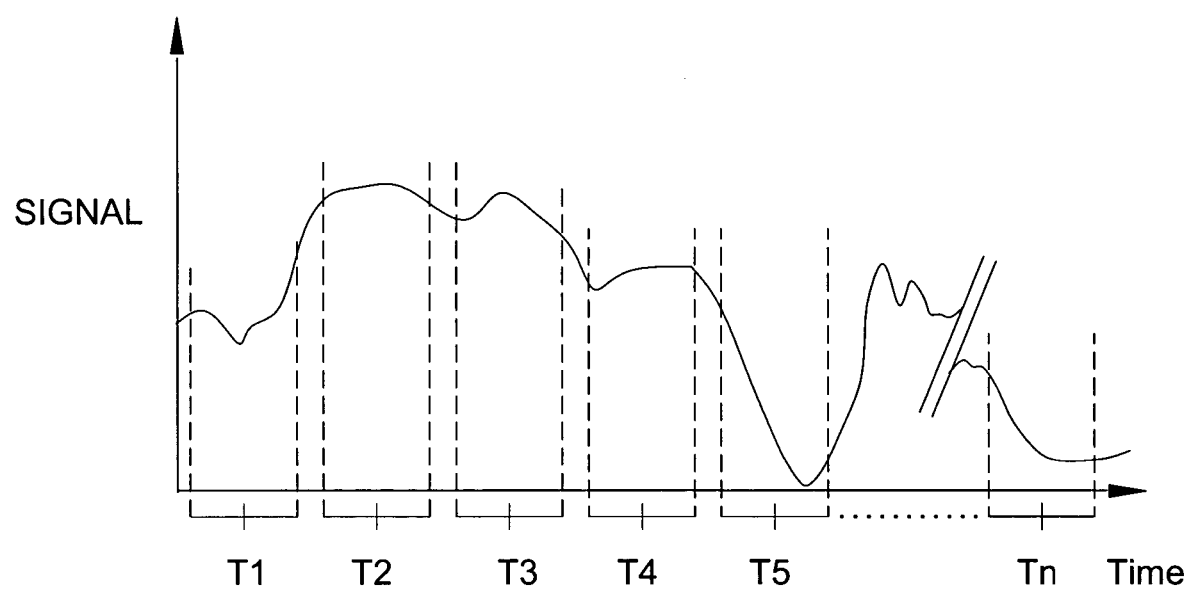
FIG. 3A is schematic description of a succession of discrete time slices implemented in the method of the present invention.
Figure 3B:
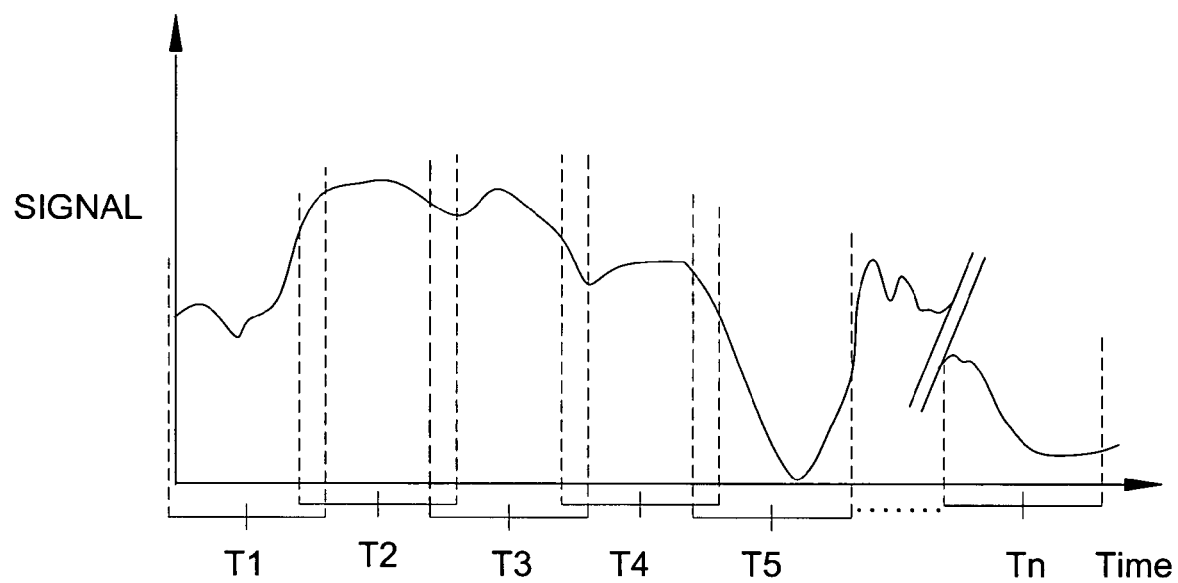
FIG. 3B is a schematic description of overlapping discrete time slices implemented in the method of the present invention.

A succession of discrete time slices as implemented in the present invention is described schematically in FIGS. 3A-B to which reference is now made. Discrete slices of time, $T_1$, $T_2 \ldots T_n$, are typically equal in length, and the center of all of which is uniformly spaced on the time axis. These discrete slices of time, may be overlapping, as in FIG. 3B. A vector V characterizing a property of the signal over a discrete slice of time is generated, typically for each slice of time $T_1$, $T_2$ etc.

$T_1 \to V_1$ $T_2 \to V_2$

...

$T_n \to V_N$

A resulting set of n vectors is denoted by $\{Vn\}$, which is further utilized in the assessment of intricate periodicities as will be described later on. Not all the vectors of the set are necessarily utilized.

The short-term characteristics are not necessarily evaluated for each of sampled times $T_j$: the evaluation may be restricted to a subset of temporal indices applied along the duration of the signal. The size of such subset is determined by the minimal period of interest and the resolution predicted as plausible for estimating the periodicity.

Figure 4:
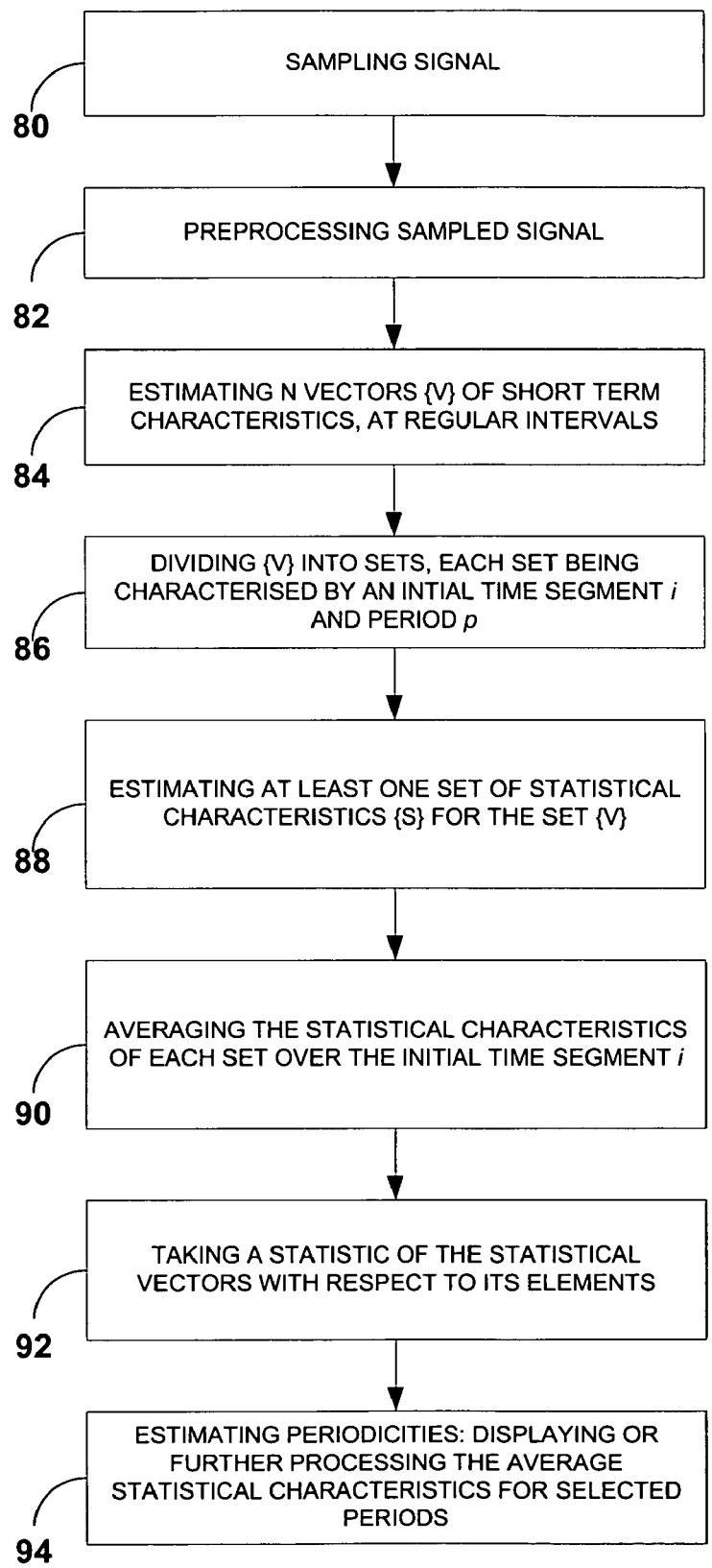
FIG. 4 is a schematic description of a general procedure of the invention.

The slice of time is defined with respect to a central time value $T_i$ and the size of the segment $\Delta$, spread equally on two sides of the central time value. A generalized procedure of the invention is described with reference to FIG. 4, which is a schematic sequence diagram of the main steps carried out in the implementation of one preferred embodiment of the invention. In step 80 the input signal is sampled at a sample rate Fs. The sampled signal is thereafter subjected to preprocessing in step 82. Then, an extraction of N vectors of short-term characteristics of size d at regular intervals, $v_j$, j=1, 2, ... N is performed in step 84, the nature of the short-term characteristics will be described below. Each short-term characteristic $v_j$ is associated with a time segment $T_j$ around which it is evaluated. These short-term characteristics $\{v\}$ are thereafter divided into sets in step 86, such that each set $\{v^{ip}\}=\{v_j|j=i+mp, m=0, 1, 2 \ldots N/p\}$, is characterized by the initial time i and a period, p. Then, in the step 88 one or more sets of statistical characteristics, $\{S^{ip}\}$ for the sets $\{v^{ip}\}$ are estimated. Since the characteristics in the set may depend on the initial time segment Ti, in step 90 each characteristic is preferably averaged with respect to the various initial time segments, Ti, i=0, 1, 2, ... P between i=0 and the corresponding period p. Then, in step 92, each of the vectors in the set $\{S^P\}$ is reduced to one number $\sigma^p$, e.g., by taking a statistic (such as the mean or the variance) of the vector with respect to its elements. The output of the system is the vector $\sigma=(\sigma^1, \sigma^2, \sigma^3 \ldots \sigma^{P\text{-}max})$, which can reveal intricate periodicities. Then in stage 94, the vector is further manipulated for displaying or processing.

Within the pre-processing stage, the signal can be subjected to de-noising, for example, by using a wavelet denoising method as described by S. Durand, J. Froment, in Artifact Free Signal De-noising with Wavelets, in: Proceedings of ICASSP 2001, 2001, IEEE 26th International Conference on Acoustics, Speech, and Signal Processing. In addition, band-pass filtering using finite-impulse response (FIR) or infinite impulse response (IIR), re-sampling to other sampling rate or any other pre-processing procedure can be applied that would render the signal more appropriate to further processing in accordance with the method described in the present invention. At the next stage, a set of time intervals, preferably overlapping, is selected, as illustrated in FIG. 3B to which reference is again made.

The short-term characteristics, produced in step 84 of the procedure is typically the short-time spectra of the signal. Methods for evaluating the short-term spectra of a signal are described, e.g., by Leon Cohen, in: "Time-Frequency Analysis", Analysis (Prentice-Hall Signal Processing, Pearson Education POD; 1st edition January 1995.

The statistical characteristics that are estimated for the set $\{v\}$ are for example average, standard deviation, and combinations of higher-order moments, such as the Skew and the Kurtosis, etc. These statistical characteristics are preferably evaluated with respect to each element in the vectors $\{v^{ip}\}$ of the short-term characteristics. For example, in case in which the statistical characteristic is the mean, we have, for the k-th element of $S^{ip}$ the equation:

$$S^{ip}(k) = \frac{p}{N} \sum_{m=0}^{N/P} V_{i+mp}(k)$$

Further averaging the characteristic with respect to the initial time segments in step 90 a generalized equation is formed:

$$S^p(k) = \frac{1}{p} \frac{p}{N} \sum_{i=0}^{P} \sum_{m=0}^{N/P} V_{i+mp}(k) = \frac{1}{N} \sum_{i=0}^{P} \sum_{m=0}^{N/P} V_{i+mp}(k)$$

thus providing for each set of vectors that corresponds to a period p a corresponding vector which can be regarded as a "representative vector" $S^p(k)$.

In step 92, a reduction of the "representative vector" $S^p(k)$ to one number is performed. If the statistic is a mean, the reduction to one number is performed as follows:

$$\sigma^p = \frac{1}{d} \sum_{l=1}^{d} S^p(k)$$

In most cases, however, it is preferable to consider higher-order statistical moments instead of the mean.

Figure 5:
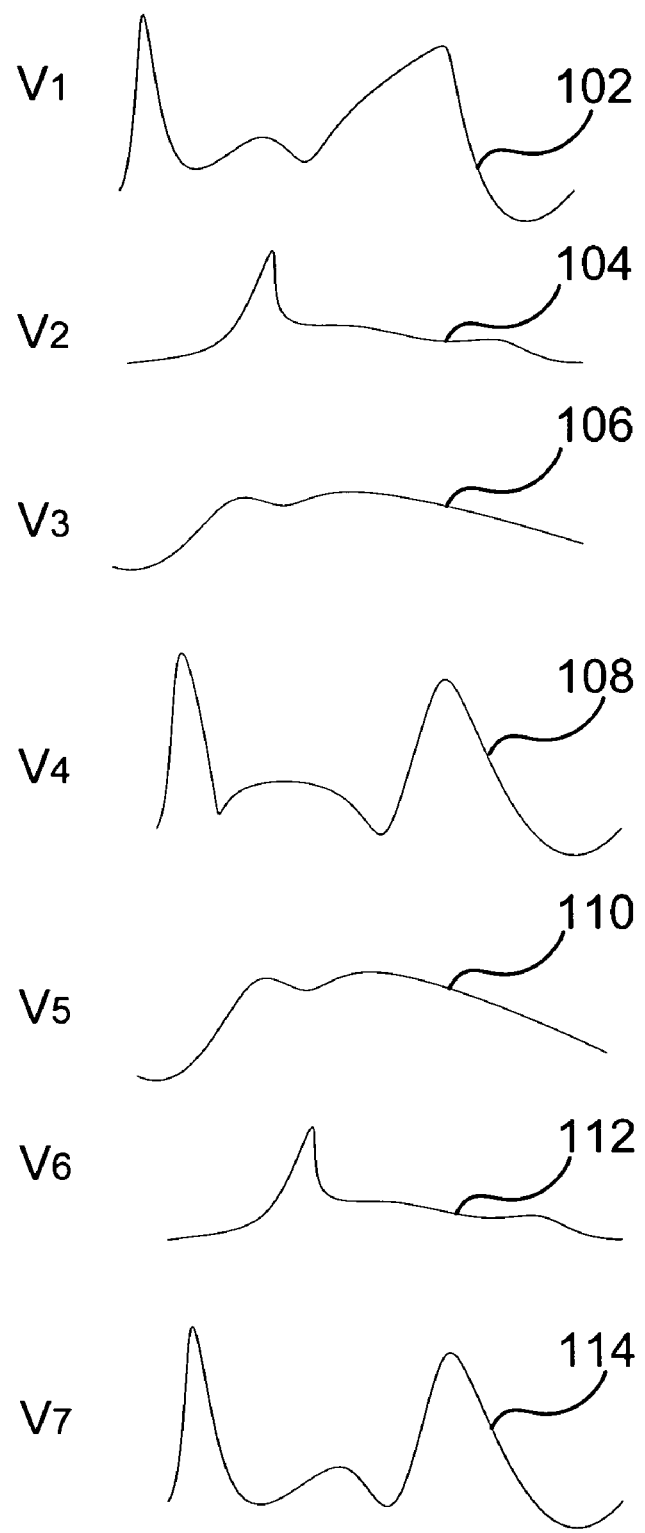
FIG. 5 is a schematic illustration of a set of characteristic vectors.

In FIG. 5 to which reference is now made, there is illustrated a set of characteristics vectors $\{V\}$. The fact that vectors $V_1$, 102 $V_4$ 108 and $V_7$ 114 are similar, is suggestive of a period in the signal having a length "3".

In order to mitigate problems arising in cases in which the distribution of the short-term vectors is multi-modal and/or does not have sufficient statistics, clustering, (vector quantization), may be performed as described by Richard O. Duda, Peter E. Hart, David G. Stork, "Pattern Classification" Wiley-Interscience; 2nd edition (2000), the contents of which are incorporated herein by reference. In a preferred embodiment of the present invention, each set $\{v\}$ of the said vectors is first clustered to two or more subsets, $\{v^{ip}\}_1, \{v^{ip}\}_2, \ldots$ etc, and a statistic is estimated with respect to each of the sets. In this case, each period is characterized by more then one statistics that are preferably sufficient, and the periodic structure is preferably characterized by the most prominent statistic.

In a preferred embodiment of the present invention, more then one temporal sequence is constructed from the original time sequence, by allowing for the tracking of more then one statistic for each cluster, and periodic structure in each of the temporal sequences are evaluated: As a simple example, in case in which the vectors are the short-term spectra, one can consider separately the high frequency part and the low-frequency part and estimate the statistics for each part separately.

Figure 6:
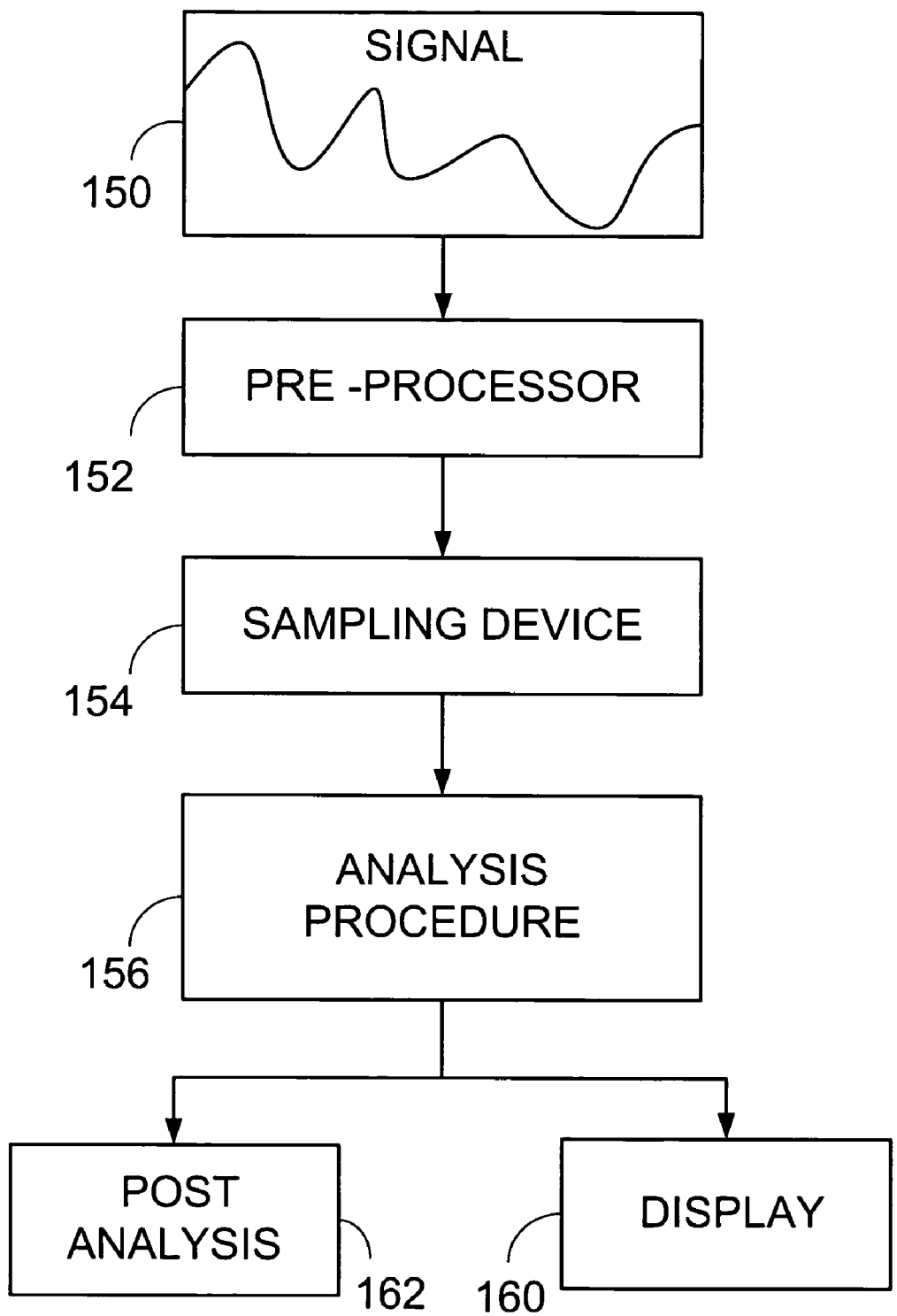
FIG. 6 is a schematic description of a system of the present invention incorporating an analysis procedure of the invention.

In FIG. 6 to which reference is now made, a system for the analysis of intricate periodic structures, constructed and operative according to a preferred embodiment of the present invention is described schematically in the form of a block diagram. Input signal 150 is subjected to a pre-processing by an analog pre-processor 152. The signal is then sampled and digitized by a sampling device 154, such as an analog to digital circuit. The digitized signal serves as an input to an analysis procedure 156 such as a one described above, in FIG. 4, and provides for an estimation of periodicities. The results of the analysis procedure 156 are thereafter presented to the user using the display 160 and/or subjected to further analysis by implementing a different analysis procedure 162. The procedures 156 and 162 are typically implemented in computerized processors based on DSP or RISC chipsets.

Preferably, the information is represented in terms of frequencies rather than periods. Such can be accomplished by performing a Fourier transform on the periodic estimation. Another way to achieve frequency representation is by assigning the amplitude of the period $\Delta T$ to the corresponding frequency $F=1/\Delta T$.

Figure 7:
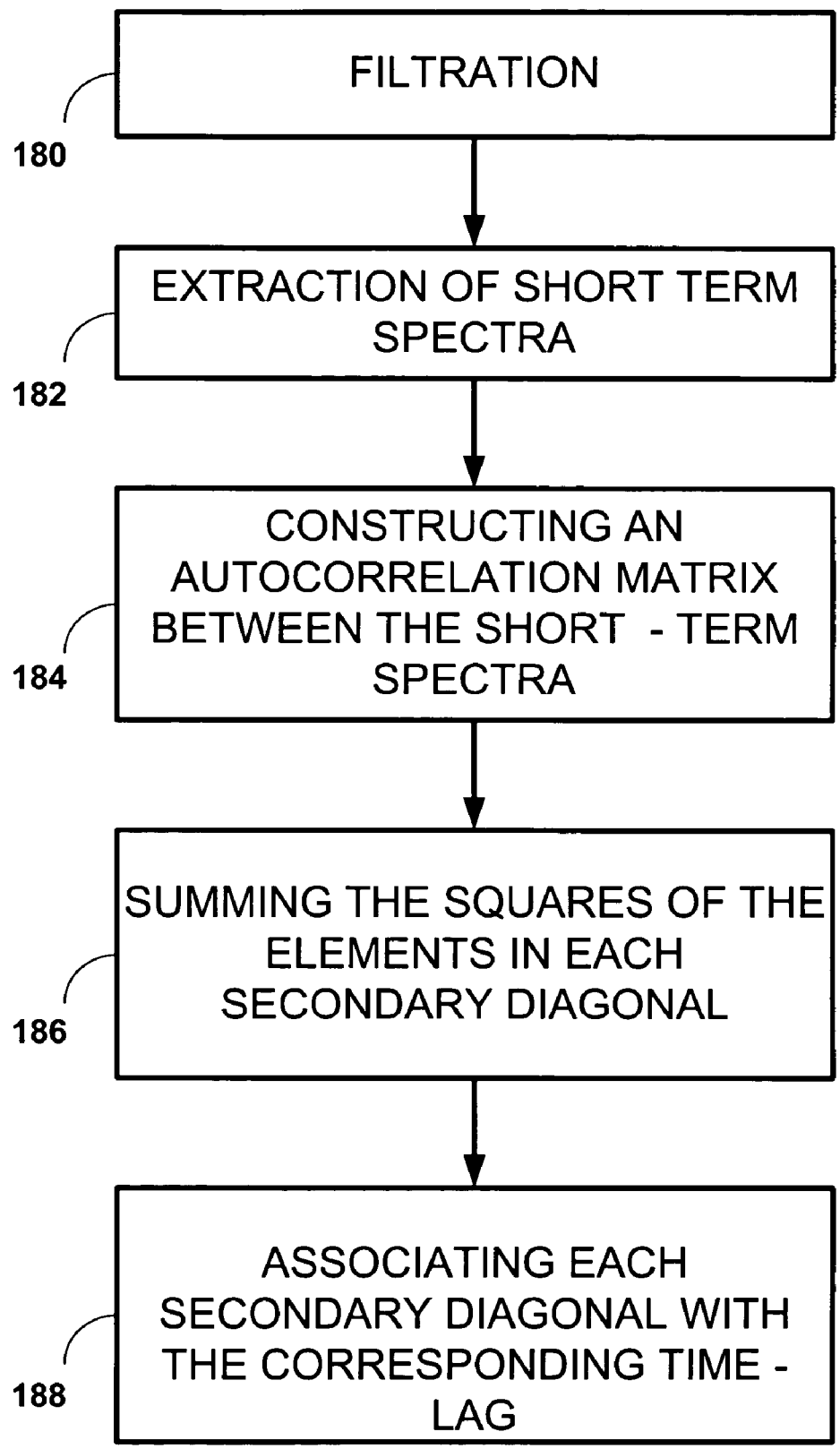
FIG. 7 is a schematic sequential description of a specific procedure for estimating periodicities in a signal whereby an autocorrelation matrix between the short-term spectra is constructed and used to indicate levels of autocorrelation in each of the spectra of an ordered sequence of time intervals.

In FIG. 7, to which reference is now made, there is illustrated a specific procedure for estimating periodicities, operative according to a preferred embodiment of the present invention. The digitized raw signal, is first pre-processed, using a band-pass filter on a wide-band signal, in step 180. Short-term spectra are thereafter obtained in step 182. At this stage, a spectrum S(t) can be associated with a subset of temporal indices along the duration of the signal. This subset is determined by the minimal period of interest and the resolution predicted as fit for estimating the periods. Then, at step 184 the auto-correlation matrix, A, between the short-term spectra is constructed, where $A_{ij}$, the ij-th element of the matrix, is the scalar product between the spectrum at time $t_i$, $s_i$ and the spectrum at time $t_j$, $s_j$:

$$A_{ij}=S(t_i)S(t_j)\equiv s_i s_j$$

$$A = \begin{pmatrix} s_1 s_1, s_1 s_2, s_1 s_3, s_1 s_4, \ldots \\ s_2 s_1, s_2 s_2, s_2 s_3, s_2 s_4, \ldots \\ s_3 s_1, s_3 s_2, s_3 s_3, s_3 s_4, \ldots \\ s_4 s_1, s_4 s_2, s_4 s_3, s_4 s_4, \ldots \end{pmatrix}$$

At step 186, the squares of the elements in each secondary diagonal are summed. Then, at step 188, the total sum-square of each secondary diagonal is associated with the generalized amplitude of the corresponding period.

The short-term spectra produced at step 182 are estimated preferably using the Welch periodogram method with Hanning window (Welch, P. D., "The Use of Fast Fourier Transform for the Estimation of Power Spectra: a Method Based on Time Averaging over Short, Modified Periodograms" IEEE Transactions on Audio and Electroacoustics, Vol. AU-15, No 2., June1967 pp. 70-73). Alternatively, short-term spectra are obtained using the Continuous-Wavelets-Transform (CWT), described, for example, by Christopher Torrence and Gilbert Compo, in: "A Practical Guide to Wavelet Analysis", Bulletin of the American Meteorological Society, v.79, no.1, p.61-78. January 1998

The main diagonal of the matrix produced at step 184 defines the correlation between the spectrum and itself (i.e., the square of the spectrum). Similarly, each of the auxiliary diagonals of the matrix includes elements that are correlations between spectra with a constant time difference, where the difference depends on the order of the diagonal. For example, the diagonal of order "1" contains the elements $S_1 S_2, S_2 S_3, S_3 S_4 \ldots$ i.e., the spectra whose time difference is $\Delta t$ (where $\Delta t$ is the difference between the times in which two consecutive spectra where evaluated). Similarly, the diagonal of order 2 contains spectra whose time difference is $2\Delta t$, etc. The various statistics (mean, variance, skew, kurtosis, entropy etc.) of the elements in each diagonal can be used to give an indication regarding the level of the generalized auto-correlation in the corresponding time-interval, and therefore can be used in order to detect subtle periodicities within the signal.

The methods and apparatus disclosed herein been described in a manner sufficient to enable persons of ordinary skill in the art to readily adapt commercially available hardware and software as may be needed to reduce any of the embodiments of the present invention to practice without undue experimentation and using conventional techniques. The skilled person will appreciate that the above combinations are not exhaustive, and all reasonable combinations of the above features are hereby included in the present disclosure.

While the present invention has been described with reference to a few specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

The invention claimed is:

1. A method for discerning periodicities in signals, comprising the succession of steps of:
    sampling and pre-processing of a raw-signal in discrete succession of equally spaced slices of time, the sampling and pre-processing being respectively executed by a sampling device and an analog pre-processor;
    generating short-term characteristics vectors for such slice of time;
    grouping said-short term characteristics vectors into sets;
    obtaining at least one representative vector for each of said sets of short-term characteristics vectors; and
    estimating periodic structures using said representative vectors,
    wherein said generating, grouping, obtaining, and estimating are executed by computerized processors.

2. A method for discerning periodicities in signals as in claim 1, wherein said short-term characteristics vectors are grouped into sets each having an initial time and a period, and further:
    reducing each of said at least one of said representative vectors into one number respectively;
    constructing a vector of the plurality of said numbers; and
    estimating periodicities in said signal,
    wherein said reducing, constructing, and estimating periodicities are executed by at least one computerized processor.

3. A method for discerning periodicities in signals as in claim 2, wherein said reducing is achieved by estimating at least one statistic of said vector with respect to its elements.

4. A method for discerning periodicities in signals as in claim 3, wherein said at least one statistic is selected from a group containing mean, variance, skew, kurtosis, and entropy.

5. A method for discerning periodicities in signals as in claim 1, wherein said short-term characteristics are the short-term spectra of the signal.

6. A method for discerning periodicities in signals as in claim 1, wherein said short-term characteristics are the short-term continuous-wavelets-transform (CWT) of the signal.

7. A method for discerning periodicities in signals as in claim 1, wherein each statistical characteristic of a corresponding set of vectors is averaged with respect to the initial time segment of the set of characteristic.

8. A method for discerning periodicities in signals as in claim 1 that further comprises the steps of:
dividing the set of vectors into at least two clusters;
obtaining a representative vector for each of the clusters;
reducing each representative vector to one number; and
taking the largest number as the output number,
wherein said dividing, obtaining a representative vector, and taking are executed by at least one computerized processor.

9. A method for discerning periodicities in signals as in claim 1, wherein said short-term characteristics vectors are grouped into sets each having an initial time and a period, and further:
reducing each said representative vector of at least one set of said sets of short-terms vectors into a number;
constructing at least two vectors of a plurality of said numbers; and
estimating periodicities in each of the said vectors,
wherein said reducing, constructing, and estimating periodicities are executed by at least one computerized processor.

10. A method for discerning periodicities in signals as in claim 9, wherein reducing said representative vectors of said at least one set of vectors into at least two numbers is achieved using a method comprising the succession of steps of:
dividing the set of vectors into at least two clusters; and
obtaining a representative vector with respect to each of said clusters.

11. A method for discerning periodicities in signals, comprising the steps of:
sampling a signal of interest using a sampling device;
pre-processing said sampled signal using an analog pre-processor;
obtaining short-term spectra of said signal at equally spaced in slices of time;
constructing an autocorrelation matrix between said short term spectra; and
associating each secondary diagonal of said matrix with a time lag,
wherein said obtaining, constructing, and associating are executed by computerized processors.

12. A method for discerning periodicities in signals as in claim 11, wherein at least one statistic of the elements of said diagonals is used to assess the auto-correlation along a diagonal.

13. A method for discerning periodicities in signals as in claim 12, wherein said at least one statistic is selected from a group containing mean, variance, skew, kurtosis, and entropy.

14. An apparatus for estimating periodicities in a signal, comprising:
an analog preprocessor that processes a sampled signal in discrete succession of equally spaced slices of time, using a band-pass filter on a wide-band signal; and
one or more processors that
generate short-term characteristics vectors for such slice of time,
group the short term characteristics vectors into set;
obtain at least one representative vector for each of said sets of short-term characteristics vectors, and
estimating of periodic structures using said representative vectors.

* * * * *